US009340588B2

(12) United States Patent
Sanchez Garcia et al.

(10) Patent No.: US 9,340,588 B2
(45) Date of Patent: May 17, 2016

(54) **PEPTIDE SECRETED BY *LACTOBACILLUS PLANTARUM* WITH IMMUNOMODULATING FUNCTION**

(75) Inventors: Borja Sanchez Garcia, Villaviciosa (ES); Abelardo Margolles Barros, Villaviciosa (ES); David Bernardo Ordiz, Harrow (GB); Stella C. Knight, Harrow (GB); Hafid Omar, Harrow (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 14/343,197

(22) PCT Filed: Sep. 7, 2012

(86) PCT No.: PCT/ES2012/070643
§ 371 (c)(1),
(2), (4) Date: May 29, 2014

(87) PCT Pub. No.: WO2013/034795
PCT Pub. Date: Mar. 14, 2013

(65) Prior Publication Data
US 2014/0296480 A1    Oct. 2, 2014

(30) Foreign Application Priority Data
Sep. 7, 2011  (ES) .................................. 201131469

(51) Int. Cl.
*C07K 14/335* (2006.01)
*A23L 1/305* (2006.01)
*A61K 38/00* (2006.01)

(52) U.S. Cl.
CPC ............. *C07K 14/335* (2013.01); *A23L 1/3053* (2013.01); *A61K 38/00* (2013.01)

(58) Field of Classification Search
CPC ..... A23L 1/3053; A61K 38/00; C07K 14/335
See application file for complete search history.

(56) References Cited

FOREIGN PATENT DOCUMENTS

| EP | 0734264 | 2/2004 | |
|---|---|---|---|
| FR | 2848115 | 12/2002 | |
| FR | 2848115 A1 | 6/2004 | |
| WO | WO 2006/110088 A1 | 10/2006 | |
| WO | WO 2006110088 | 10/2006 | |
| WO | WO 2009130423 A2 * | 10/2009 | ............... C12N 1/20 |
| WO | WO 2009/138092 A1 | 11/2009 | |
| WO | WO 2009138092 | 11/2009 | |
| WO | WO 2011/052996 A2 | 5/2011 | |
| WO | WO 2011052996 | 5/2011 | |

OTHER PUBLICATIONS

UniProt Protein Database, Protein Accession D7V879, LysM domain Protein, amino acid sequence on p. 2, accessed on Mar. 14, 2015.*

English Translation of the Description and Claims of WO2009130423 A2, accessed on Jul. 28, 2015.*
Adams et al., "IgG Antibodies Against Common Gut Bacteria Are More Diagnostic for Crohn's Disease Than IgC Against Mannan or Flagellin," *American Journal of Gastroenterology*, 2008, 103:386-396.
Bagwell et al., "HyperLog—A Flexible Log-Like Transform for Negative, Zero, and Positive Valued Data," *Cytometry*, 2005, 64:34-42.
de Vries et al., "Lactobacillus Plantarum—Survival, Functional and Potential Probiotic Properties in the Human Intestinal Tract," *International Dairy Journal*, 2006, 16:1018-1028.
Feng et al., "Adaptive Immunity in the Host-Microbiota Dialog," *Mucosal Immunology*, 2010, 4:15-21.
Hart et al., "Characteristics of Intestinal Dendritic Cells in Inflammatory Bowel Diseases," *Gastroenterlogy*, 2005, 129:50-65.
Heuvelin et al., "Mechanisms Involved in Alleviation of Intestinal Inflammation by Bifidobacterium Breve Soluble Factors," *PLoS ONE*, 2009, 4:e5184.
Lebeer et al., "Host Interactions of Probiotic Bacterial Surface Molecules: Comparison with Commensals and Pathogens," *Nature Reviews Microbiology*, 2010, 8:171-84.
Ng et al. "A Novel Population of Human CD56+ Human Leucocyte Antigen D-related (HLA-DR+) Colonic Lamina Propria Cells is Associated with Inflammation in Ulcerative Colitis," *Clinical & Experimental Immunology*, 2009, 158:205-218.
Rescigno et al., "Dendritic Cells Express Tight Junction Proteins and Penetrate Gut Epithelial Monolayers to Sample Bacteria," *Nature Immunology*, 2001, 2:361-367.
Rijkers et al., "Guidance for Substantiating the Evidence for Beneficial Effects of Probiotics Current Status and Recommendations for Future Research," *The Journal of Nutrition*, 2010, 140:671S-676S.
Sanchez et al., "Exported Proteins in Probiotic Bacteria: Adhesion to Intestinal Surfaces, Host Immunomodulation and Molecular Cross-Talking with the Host," *Immunol Med Microbiol*, 2008, 54:1-17.
Stockinger et al., "Differentiation and Function of Th17 T Cells," *Current Opinion in Immunology*, 2007, 19:281-286.
Tallon et al., "Isolation and Characterization of Two Exopolysaccharides Produced by Lactobacillus Plantarum EP56," *Research in Microbiology*, 2003, 154:705-712.

(Continued)

*Primary Examiner* — James H Alstrum Acevedo
*Assistant Examiner* — Erinne Dabkowski
(74) *Attorney, Agent, or Firm* — Mueting, Raasch & Gebhardt, P.A.

(57) ABSTRACT

Among the fewer than 10 proteins primarily secreted by the species *Lactobacillus plantarum*, there is one of 30 kDa that contains an internal fragment without cleavage sites for the most important intestinal proteases and characterized by having a serine and threonine content of at least 50%. The genetic information encoded in this fragment, designated ST peptide, has been used for producing and purifying the peptide, thus making it possible to conduct various tests in vitro.
To summarize, the ST peptide is considered to promote the process of immunologic ignorance of our gastrointestinal immune system toward the commensal bacteria of our gastrointestinal tract, thus favoring the mechanisms of oral tolerance. Therefore the ST peptide could be used in immunotherapy, especially in the context of certain autoimmune diseases and certain inflammatory diseases.

18 Claims, 11 Drawing Sheets

(56) References Cited

OTHER PUBLICATIONS

Turroni et al., "Characterization of the Serpin-Encoding Gene of Bifobacterium Breve 210B," *Applied and Environmental Microbiology*, 2010, 76:3206-3219.

Zhu et al., "CD4 T Cells: Fates, Functions and Faults," *Blood*, 2008, 112:1557-1589.

Sanchez et al., 2009, Identification of Novel Proteins Secreted by Lactobacillus Plantarum that Bind to Mucin and Fibronectin, *J. Mol. Microbiol. Biotechnol.* 3:158-162.

Hevia et al., 2013, An Extracellular Serine/Threonine-Rich Protein from Lactobacillus Plantarum NCIMB 8826 Is a novel Aggregation-Promoting Factor with Affinity to Mucin, *Appl. Environ. Microbiol.* 79(19):6059-6066.

\* cited by examiner

A.

SEQ ID NO: 2

B.

ST peptide
GEVDGDSTTTTSTSTQTTQQTTTTQSSAQTSQTQAQPSQASQTQSSQTQTSKPAAQTTQTSSSTSNYHHHHHH

SEQ ID NO: 1

FIG. 3
A.
SEQ ID NO: 3
B.
SEQ ID NO: 4
ABBREVIATIONS
* Ch-hi → Cleavage of chymotrypsin (high specificity) (C-terminal of the sequence [FYW], except before P)
* Ch-lo → Cleavage of chymotrypsin (low specificity) (C-terminal of the sequence [FYWML], except before P)
* Pn1.3 → Pepsin (pH1.3)
* Pn2 → Pepsin (pH>2)
* Tryps → Trypsin FIG. 4
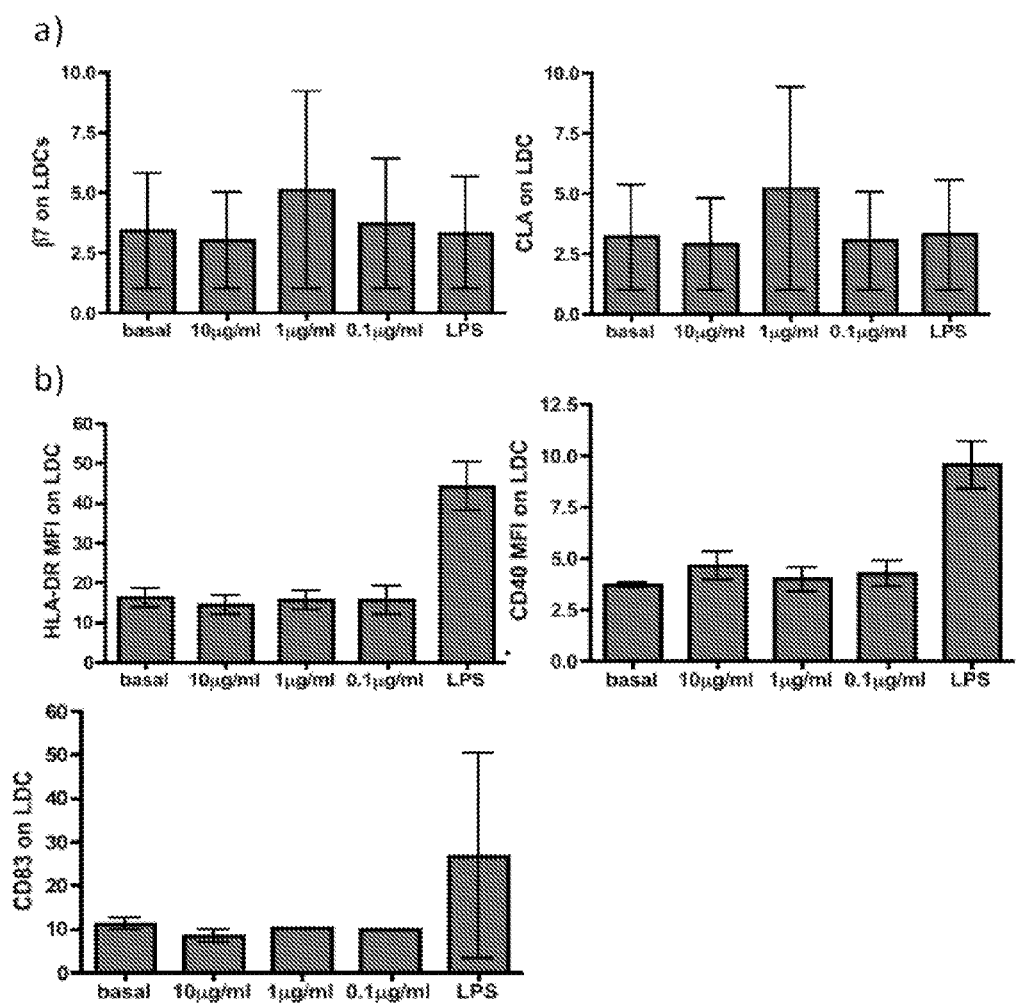
FIG. 5

FIG. 8
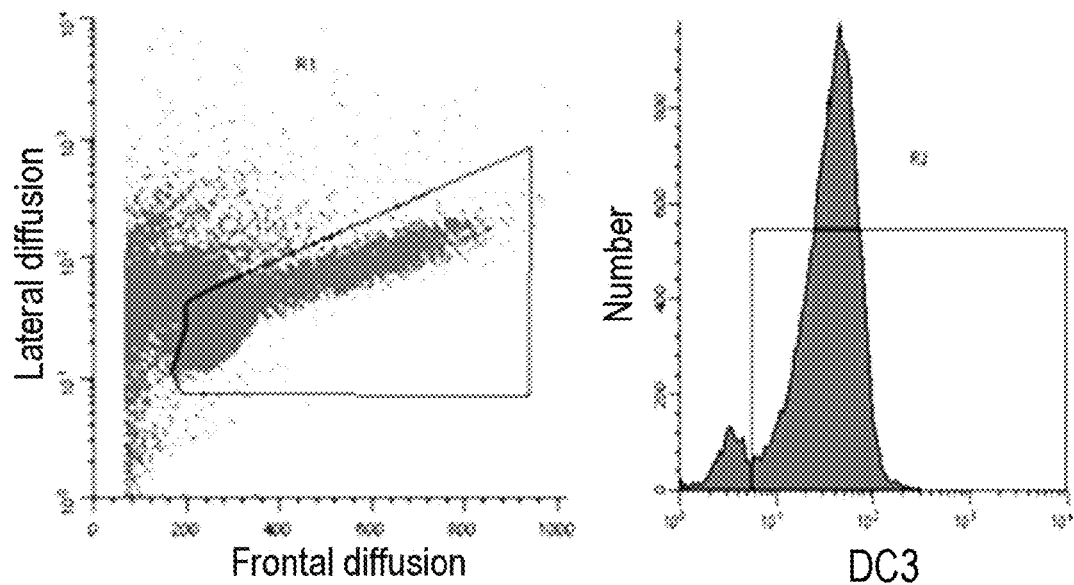
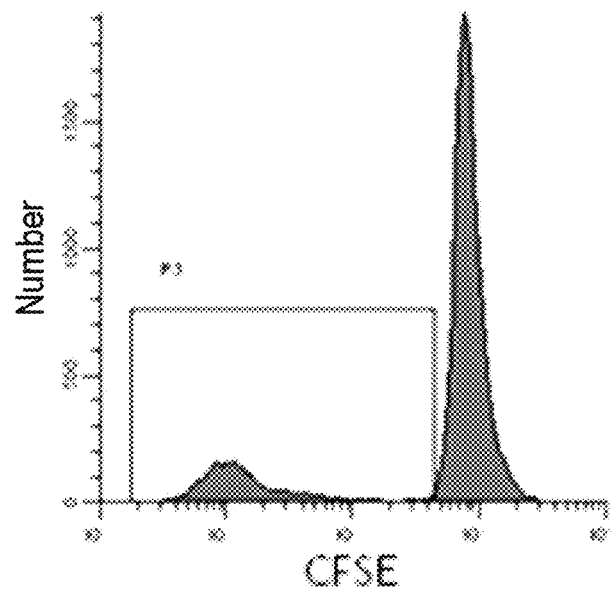

FIG. 10

FIG. 14
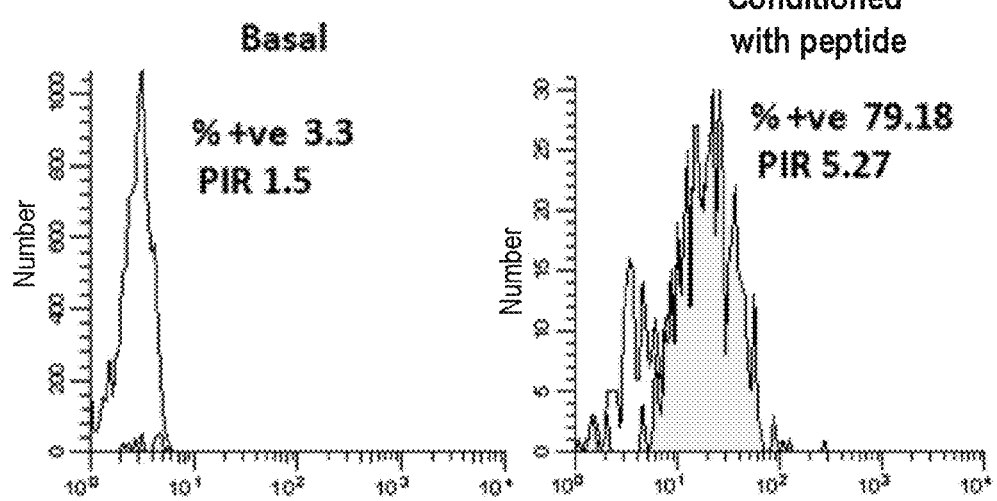
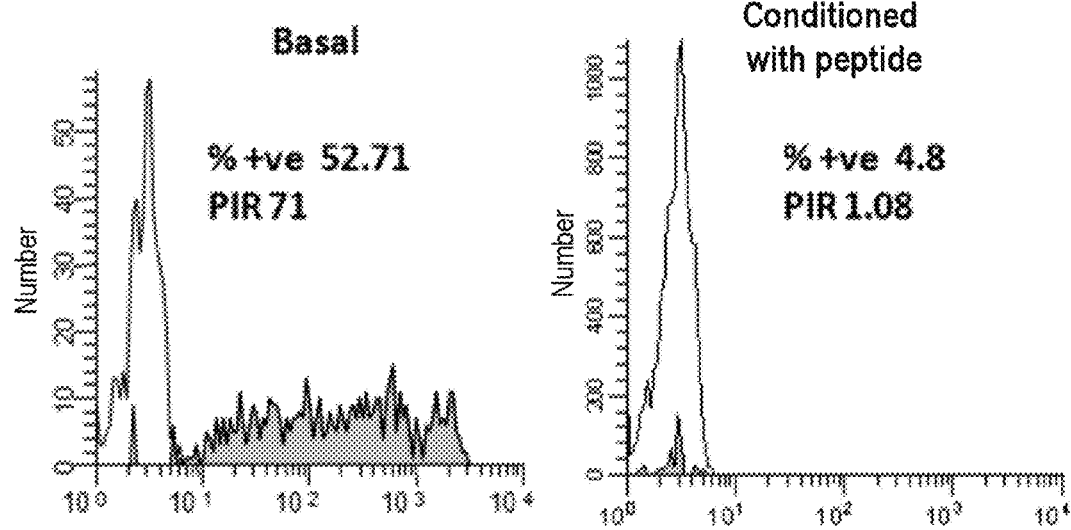

SEQUENCE LISTING

<160> NUMBER OF SEQ ID NOS: 4

<210> SEQ ID NO 1

-continued

```
<211> LENGTH: 73
<212> TYPE: PRT
<213> ORGANISM: Lactobacillus plantarum
<220> FEATURE:
<221> NAME/KEY: MISC_FEATURE
<222> LOCATION: (1)..(73)
<223> OTHER INFORMATION: ST peptide sequence

<400> SEQUENCE: 1

Gly Glu Val Asp Gly Asp Ser Thr Thr Thr Ser Thr Ser Thr Gln
1               5                   10                  15

Thr Thr Gln Gln Thr Thr Thr Thr Gln Ser Ser Ala Gln Thr Ser Gln
                20                  25                  30

Thr Gln Ala Gln Pro Ser Gln Ala Ser Gln Thr Gln Ser Ser Gln Thr
            35                  40                  45

Gln Thr Ser Lys Pro Ala Ala Gln Thr Thr Gln Thr Ser Ser Ser Thr
        50                  55                  60

Ser Asn Tyr His His His His His His
65                  70

<210> SEQ ID NO 2
<211> LENGTH: 66
<212> TYPE: PRT
<213> ORGANISM: Lactobacillus plantarum
<220> FEATURE:
<221> NAME/KEY: MISC_FEATURE
<222> LOCATION: (1)..(66)
<223> OTHER INFORMATION: Amino acids 70-135 of protein D1

<400> SEQUENCE: 2

Glu Val Asn Gly Asp Ser Thr Thr Thr Ser Thr Ser Thr Gln Thr
1               5                   10                  15

Thr Gln Gln Thr Thr Thr Thr Gln Ser Ser Ala Gln Thr Ser Gln Thr
                20                  25                  30

Gln Ala Gln Pro Ser Gln Ala Ser Gln Thr Gln Ser Ser Gln Thr Gln
            35                  40                  45

Thr Ser Lys Pro Ala Ala Gln Thr Thr Gln Thr Ser Ser Ser Thr Ser
        50                  55                  60

Asn Tyr
65

<210> SEQ ID NO 3
<211> LENGTH: 60
<212> TYPE: PRT
<213> ORGANISM: Lactobacillus plantarum
<220> FEATURE:
<221> NAME/KEY: MISC_FEATURE
<222> LOCATION: (1)..(60)
<223> OTHER INFORMATION: Amino acids 61-120 of protein D1

<400> SEQUENCE: 3

Asn Leu Ile Leu Val Gly Gln Gln Leu Glu Val Asn Gly Asp Ser Thr
1               5                   10                  15

Thr Thr Ser Thr Ser Thr Gln Thr Thr Gln Gln Thr Thr Thr Thr
                20                  25                  30

Gln Ser Ser Ala Gln Thr Ser Gln Thr Gln Ala Gln Pro Ser Gln Ala
            35                  40                  45

Ser Gln Thr Gln Ser Ser Gln Thr Gln Thr Ser Lys
        50                  55                  60

<210> SEQ ID NO 4
<211> LENGTH: 60
```

```
<212> TYPE: PRT
<213> ORGANISM: Lactobacillus plantarum
<220> FEATURE:
<221> NAME/KEY: MISC_FEATURE
<222> LOCATION: (1)..(60)
<223> OTHER INFORMATION: Amino acids 121-180 of protein D1

<400> SEQUENCE: 4

Pro Ala Ala Gln Thr Thr Gln Thr Ser Ser Ser Thr Ser Asn Tyr Ser
1               5                   10                  15

Asn Asn Gly Ser Asp Ser Ala Ala Lys Ala Trp Ile Ala Gly Lys Glu
            20                  25                  30

Ser Gly Gly Ser Tyr Ser Ala Arg Asn Gly Gln Tyr Ile Gly Lys Tyr
        35                  40                  45

Gln Leu Ser Ala Ser Tyr Leu Asn Gly Asp Tyr Ser
    50                  55                  60
```

PEPTIDE SECRETED BY *LACTOBACILLUS PLANTARUM* WITH IMMUNOMODULATING FUNCTION

GOVERNMENT FUNDING

The work leading to this invention has received funding from the European Community's Seventh Framework Programme (FP7/2007-2013) under grant agreement no. 235993.

This application is a U.S. National Stage Application of International Application No. PCT/ES2012/070643, filed Sep. 7, 2012, which was published in English on Mar. 14, 2013 as International Patent Publication WO 2013/034795 A1. International Application No. PCT/ES2012/070643 also claims priority to Spanish Application No. P201131469, filed Sep. 7, 2011.

SEQUENCE LISTING

This application contains a Sequence Listing electronically submitted via EFS-Web to the United States Patent and Trademark Office as an ASCII text filed entitled "US14-343197_SequenceListing_ST25.txt" having a size of 4 kilobytes and created on Jun. 16, 2014. The information contained in the Sequence Listing is hereby incorporated herein by reference and does not go beyond the disclosure in the International Application, PCT/ES2012/070643, as filed.

The present invention, which describes the use of a peptide secreted by a *lactobacillus* in human immunotherapy, relates both to the food technology sector and to medicine. It relates to the amino acid sequence (ST peptide) that could be used in immunotherapy of certain inflammatory diseases, such as inflammatory bowel disease (IBD; divided into Crohn's disease, ulcerative colitis and pouchitis) and in other pathologies where oral tolerance is compromised (as in the case of celiac disease with respect to dietary gluten). The route of administration could be inclusion in a functional foodstuff or via directed maturation of donor dendritic cells (vaccines of dendritic cells).

PRIOR ART

The human gastrointestinal tract is home to a wide variety of commensal, mutualist and pathogenic bacteria and is precisely where there is one of the main points of contact between bacteria and the immune system. This set of bacteria contributes to a large extent to the set of antigens or foreign substances together with the antigens in the diet against which, in normal conditions, the immune system would react with the aim of eliminating them, as occurs in systemic immunity. However, in the intestinal compartment this does not occur at all like this, and instead a mechanism of immunologic tolerance is deployed against said antigens, called oral tolerance, intended to maintain homeostasis of the mucosa (Feng and Elson (2010) Adaptive immunity in host—microbiota dialog. *Muc. Immunol.* 4, 15-21). In certain circumstances this homeostasis is lost and the immune system reacts abnormally against the intestinal microbiota, with development of more or less severe inflammatory processes such as inflammatory bowel disease (IBD) or against some antigens in the diet (as in the case of gluten in celiac disease). Moreover, the relation that exists between certain autoimmune diseases and deregulation in the composition of the intestinal microbiota is also known (Adams et al. (2008) IgG antibodies against common gut bacteria are more diagnostic for Crohn's Disease than IgG against mannan or flagellin. *Am. J. Gastroenterol.* 103, 386-396).

The process of tolerance to the intestinal microbiota is mediated, in large part, by two cellular types which, incorporated in the intestinal mucosa, are responsible for the correct processing and recognition of the antigens originating from the intestinal microbiota. These are the T lymphocytes and the dendritic cells (DCs). The DCs are phagocytic cells specialized in the processing and presentation of antigens; in the case of the intestinal DCs they play an essential role in recognition of the microorganisms that are present there, putting out pseudopodia between the enterocytes of the intestinal epithelium toward the lumen (Rescigno et al. (2001) Dendritic cells express tight junction proteins and penetrate gut epithelial monolayers to sample bacteria. *Nat Immunol.* 2, 361-367). The DCs engulf the bacterial particles and process them, undergoing a series of changes called maturation and displaying these bacterial antigens on their surface, so that they can be recognized by other cells of the immune system. This change, moreover, is accompanied by a series of phenotypic alterations in the DCs, such as the production of certain cytokines. The DCs are, in their turn, crucial for the proliferation and differentiation of the T lymphocytes into effector cells of type Th1 (induce a pro-inflammatory response), Th2 (induce an anti-inflammatory response) or Th17 (are involved in the protection of surface tissues against infections), or else into regulatory cells (Treg) (Zhu and Pau (2008) CD4 T cells: fates, functions, and faults. *Blood* 112, 1557-1569). Complementing the DCs, the T lymphocytes are the cells responsible for the cellular immune response.

Some strains belonging to the lactic acid group of bacteria are considered to be probiotic, since they are capable of modulating the composition of the intestinal microbiota favorably, with beneficial effects on human health (Rijkers, G. T. et al. (2010) Guidance for substantiating the evidence for beneficial effects of probiotics: current status and recommendations for future research. *J. Nutr.* 140, 671S-676S). In recent years, various research teams have been accumulating scientific evidence that suggests that certain extracellular components might be responsible for some of the beneficial effects attributed to probiotics. This makes more sense if it is borne in mind that in normal conditions, in healthy individuals, the microbiota is not in direct contact with the layer of enterocytes and/or the DCs. In fact, the microbiota is embedded in the protective layer of mucus that covers the epithelial layer of the intestine. It is therefore plausible that these beneficial effects of probiotics are not due to direct interaction of the bacteria with the DCs. Conversely, the probiotics might perform their function by producing certain components that can cross the layer of mucus, facilitating capture of them by the DCs. Among these extracellular components, we may mention exopolysaccharides, teichoic acids, indoles and the surface and extracellular proteins (Lebeer et al. (2010) Host interactions of probiotic bacterial surface molecules: comparison with commensals and pathogens. *Nat. Rev. Microbiol.* 8, 171-84). The latter are defined as the group of proteins that are secreted during bacterial growth and that are released to the medium surrounding them (Sánchez et al. (2008) Exported proteins in probiotic bacteria: adhesion to intestinal surfaces, host immunomodulation and molecular cross-talking with the host. FEMS *Immunol. Med. Microbiol.* 54, 1-17). At present, the extracellular proteins constitute an active area of research for identification and characterization of the molecular mechanisms of action of probiotics.

The extracellular proteins can be divided into two main groups. The first comprises those proteins that have a signal peptide that is located in their N-terminal portion and guides the pre-protein to the secretion machinery, via which it is secreted to the medium. The second group comprises those proteins which, in addition to a signal peptide, have cell surface binding domains, and are released to the medium during the process of renewal of the bacterial wall. Finally, some authors identify a third group of extracellular proteins, comprising proteins of the central metabolism, without secretion domains, and for which the mechanism responsible for their secretion to the extracellular environment is unknown.

The systems for secreting proteins are highly conserved within the Eubacteria division. These systems are particularly well characterized in Gram-negative bacteria, where at least seven systems are identified (types 1-6 and the system of "twin arginines") (Sibbald and van Dijl (2009) Bacterial secreted proteins: secretory mechanisms and role in pathogenesis. Ed. Wooldridge, Caister Academic Press). In Gram-positive bacteria, the taxonomic group that comprises the majority of probiotic strains, the extracellular proteins would be exported by similar systems.

Until now, bioinformatics has been the tool used for identifying extracellular proteins in probiotics, and only a small proportion have been well identified or characterized experimentally. Among the extracellular proteins produced by the bifidobacteria, we may mention the serine protease inhibitor (serpin), produced by various species of bifidobacteria (Turroni et al. (2010) Characterization of the serpin-encoding gene of *Bifidobacterium breve* 210B. *Appl. Environ. Microbiol.* 76, 3206-3219). This protein efficiently inhibits both the elastases secreted by the exocrine pancreas and by the neutrophils, immune cells implicated in inflammatory processes. For this reason it has been postulated that serpin might be responsible for some of the anti-inflammatory effects of the bifidobacteria. It has also been suggested that proteins secreted by a strain of *Bifidobacterium breve* could be capable of producing soluble factors, very probably small peptides, which after interacting with the DCs would reduce the inflammatory processes at the level of the intestinal epithelium (Heuvelin et al. (2009) Mechanisms involved in alleviation of intestinal inflammation by *Bifidobacterium breve* soluble factors. *PLoS ONE.* 4:e5184).

These works are just examples of how the process of intercellular communication between bacteria and immune cells of the innate system could mediate a series of physiological responses directed at regulating the immunologic homeostasis of our intestinal mucosa, and therefore of our body. Part of this process, as shown by the results described in the present invention, could be mediated by peptides encoded within the main proteins secreted by the lactic acid bacteria present in our gastrointestinal tract.

Regarding similar patents available in the databases, we may mention patent EP95900421.9 that relates to protection of some compositions that bind specifically to colorectal cancer cells and the method of use thereof. This document describes the use of other ST peptides, in this case derivatives of a heat-stable toxin produced by a strain of the bacterium *Escherichia coli*, whose sequences do not correspond to the sequence of the peptide described in this invention. Although this document defines the "ST peptides" as the ST receptor binding peptides of between 13 and 25 amino acids, these peptides originate from *E. coli* and are included in conjugated compounds, which also comprise a radiostable active residue, and are capable of being directed specifically at metastasized colorectal cancer cells.

On the other hand, WO2009138092 refers to strain 299v of *Lactobacillus plantarum* and stresses the probiotic properties of the strain *Lb. plantarum* DSM 21379, describing the use thereof in the development of a functional foodstuff and of a medicinal product for improving cellular immunity. The functions of this microorganism that are emphasized include that of inducing the production of cytokines for improving the animal's immune system. Although this document describes how *Lb. plantarum* produces cytokines for improving the immune system, said cytokines are pro-inflammatory (IL-6).

Therefore there is currently a need to identify an ST peptide derived from proteins secreted by lactic acid bacteria, with both immunomodulating and anti-inflammatory function for treating diseases connected with deregulation of the intestinal microbiota, inflammatory diseases and/or diseases where oral tolerance is compromised.

BRIEF DESCRIPTION OF THE INVENTION

This invention describes the sequence of the ST peptide, encoded within one of the proteins secreted by a lactic acid bacterium, preferably *Lactobacillus plantarum* (so far without known function), said peptide of 30 kDa contains a fragment without cleavage sites for the most important intestinal proteases. It is also characterized by having a serine and threonine content of at least 50%. If this peptide is brought in contact with DCs obtained both from blood and from human intestinal biopsies, it is able to modulate them to a regulatory phenotype where the production of IL-12 (pro-inflammatory interleukin characteristic of antigen presenting cells) is blocked and the production of IL-10 (anti-inflammatory cytokine via blocking of the synthesis of pro-inflammatory cytokines by other immune cell types, such as the T lymphocytes) is expanded. These DCs treated with the ST peptide also acquire a different functionality since the T lymphocytes that they stimulate acquire a migratory profile directed preferentially at the skin with a profile of non-pro-inflammatory cytokines. This mechanism of action contributes actively to maintaining intestinal homeostasis not by priming the mechanisms of immunologic tolerance but instead of immunologic ignorance. Thus, the mature DCs with the ST peptide in the intestine promote secondary migration of the effector cells (T lymphocytes) to the skin, thereby hindering the establishment of an active immune response against the commensal flora in the gastrointestinal tract.

To summarize, the ST peptide promotes the mechanisms of intestinal homeostasis via its action on the DCs. Since it is capable of blocking an anti-inflammatory interleukin (IL-12) and of increasing the synthesis of an anti-inflammatory interleukin (IL-10), the ST peptide could be used in immunotherapy, in the context of certain inflammatory and autoimmune diseases, in which it is known that there is an abnormal immune response to the intestinal microbiota as well as in other pathologies where the mechanisms of oral tolerance to other antigens are lost. This would provide the scientific basis for the creation of a whole range of functional foodstuffs that would contain those molecules, produced by the probiotics, that are responsible for their beneficial action on human health.

DETAILED DESCRIPTION OF THE INVENTION

The present invention relates to an ST peptide with immunomodulating and/or anti-inflammatory properties, characterized in that:
a) it is secreted by a bacterium of the genus *Lactobacillus*,
b) its amino acid sequence has a content of between 30 and 60% of the amino acids serine and threonine, and
c) it comprises a fragment of at least 30 kDa without cleavage sites for at least one intestinal protease.

In the present invention, the term "ST peptide" refers to a peptide preferably of 73 amino acids, with immunomodulating and/or anti-inflammatory properties, that is secreted preferably by a *Lactobacillus bacterium*, preferably by *Lactobacillus plantarum*, more preferably by the strains *Lb. plantarum* NCIMB 8826, *Lb. plantarum* 299V, and *Lb. plantarum* BMCM12, whose amino acid sequence has a content of at least 50% of the amino acids serine and threonine, and comprises a fragment of at least 30 kDa without cleavage sites for at least one intestinal protease. This peptide can have at least 80-100% homology with SEQ ID No: 1, or the ortholog thereof.

In the present invention, the expression "with immunomodulating properties" refers to its capacity for modulating the response of cells of the human immune system such as the dendritic cells, which in their turn are capable of modulating the function of other immune cells such as the T lymphocytes. This modulation of the immune response comprises blocking.

In the present invention, the expression "with anti-inflammatory properties" refers to its capacity for inducing the production of interleukin 10, a potent anti-inflammatory cytokine, as well as for blocking the production of interleukin 12, a cytokine of a pro-inflammatory nature, in dendritic cells isolated both from peripheral blood and from human intestinal mucosa. Moreover, T lymphocytes matured in the presence of said dendritic cells will also acquire a profile of production of non-pro-inflammatory cytokines.

In a preferred embodiment said *Lactobacillus bacterium* is *Lactobacillus plantarum*. More preferably, the strain of said bacterium *Lactobacillus plantarum* is selected from the following group of strains: *Lb. plantarum* NCIMB 8826, *Lb. plantarum* 299V, and *Lb. plantarum* BMCM12.

In a preferred embodiment of the present invention, said ST peptide is characterized in that its amino acid sequence has at least 80-100% homology with SEQ ID No: 1. Preferably said ST peptide is characterized in that its amino acid sequence has 95% homology with SEQ ID No: 1. More preferably said ST peptide is characterized in that its amino acid sequence is SEQ ID No: 1, or the ortholog thereof.

In the present invention the term "homology" refers to the concept of "sequence homology", referring to the degree of similarity between two amino acid or nucleotide sequences.

In the present invention the term "ortholog" refers to two amino acid or nucleotide chains, derived from two different organisms, that share a high degree of homology.

In a preferred embodiment of the present invention, said ST peptide is characterized in that the intestinal protease is selected from the following group: pepsin, trypsin, chymotrypsin, and combinations thereof.

The present invention also refers to the use of said ST peptide in a method for treating and/or preventing an intestinal disorder, said method being characterized in that it comprises administering a therapeutically effective amount of the ST peptide defined above to a patient, to activate the process of immunologic ignorance or tolerance to the commensal bacteria of the intestine of said patient.

In the present invention the term "intestinal disorder" refers to any intestinal ailment where the immune system is involved either in its origin or in its treatment.

In the present invention the term "immunologic tolerance" refers to the set of induced processes whereby the immune system does not respond to an antigen, endogenous or exogenous.

In the present invention, the term "immunologic ignorance" refers to its capacity for promoting the mechanisms of intestinal homeostasis promoting not only immunologic tolerance (differentiating the dendritic cells isolated both from peripheral blood and from human intestinal mucosa toward a cytokine regulatory profile) but also priming the T lymphocytes that are stimulated with an increased capacity for migration toward skin tissues where they will not be exposed to the microbial antigens of the gastrointestinal tract.

In the present invention the expression "commensal bacteria of the patient's intestine" refers to the set of bacteria that live in the human gastrointestinal tract.

In a preferred embodiment of the present invention said intestinal disorder is an inflammatory disease, selected between an inflammatory bowel disease (IBD), or a celiac disease.

In an even more preferred embodiment of the present invention said inflammatory bowel disease (IBD) is selected from the following group: Crohn's disease, ulcerative colitis and pouchitis.

In a preferred embodiment of the present invention said intestinal disorder is caused by an autoimmune disease or a disease caused by deregulation in the composition and/or activity/metabolism of the intestinal microbiota.

In a preferred embodiment of the present invention said immunomodulating and/or anti-inflammatory properties are manifested respectively in that the administration of a therapeutically effective amount of the ST peptide to a patient comprises:

a) inducing, in the dendritic cells of said patient, the production of an anti-inflammatory and homeostatic cytokine, preferably interleukin 10 (IL-10), and/or b) blocking, in the dendritic cells of said patient, the production of a pro-inflammatory cytokine, preferably pro-inflammatory interleukin 12 (IL-12), when this is present, in addition to other pro-inflammatory cytokines such as IL-6 that are highly relevant in inflammatory bowel disease.

In an even more preferred embodiment, the method of treatment and/or prevention defined above is characterized in that said dendritic cells in their turn induce the maturation of T lymphocytes, which:

a) acquire a profile of migration to the skin, and/or b) acquire a profile of production of non-pro-inflammatory cytokines.

Preferably the profile of migration to the skin defined in a) comprises a decrease in expression of the marker of migration to intestinal mucosa integrin β7 and an increase in expression of the marker of migration to skin CLA. Preferably the profile of production of non-pro-inflammatory cytokines defined in b) comprises a decrease in the expression of pro-inflammatory cytokines IFNγ and interleukin 17 (IL-17).

In another preferred embodiment of the present invention, said administration of a therapeutically effective amount of the ST peptide is characterized in that said ST peptide is contained in a functional foodstuff (probiotic) or else in a pharmaceutical composition, preferably in the form of a capsule.

Another aspect protected by the present invention relates to a functional foodstuff, characterized in that it comprises a therapeutically effective amount of the ST peptide defined above.

In the present invention the term "functional foodstuff" refers to the set of foodstuffs which, in addition to their nutritional characteristics, confer a benefit on the consumer's health or help to avoid contracting diseases.

Another aspect protected by the present invention relates to a composition, preferably pharmaceutical, characterized in that it comprises a therapeutically effective amount of the ST peptide defined above.

In the present invention the term "pharmaceutical composition" refers to a mixture of active principles and excipients with a format suitable for use in humans.

The present invention also relates to the use of the functional foodstuff or composition defined above, to activate the process of immunologic tolerance toward the commensal bacteria of the patient's intestine.

The present invention also relates to the use of said ST peptide in a cosmetic application.

In the present invention the term "cosmetic application" refers to the use in cosmetics intended to improve the state of human skin, notably of the face.

Throughout the description and the claims, the word "comprises" and its variants are not intended to exclude other technical characteristics, additives, components or steps. For a person skilled in the art, other aims, advantages and features of the invention will become clear partly from the description and partly from the implementation of the invention. The following figures and examples are provided for purposes of illustration, and are not intended to limit the present invention.

DESCRIPTION OF THE FIGURES

FIG. 3. Theoretical cleavage sites of the main intestinal proteases on the central fragment of protein D1, identified as SEQ ID NO: 2. As can be seen (indicated with an arrow), the fragment ST does not contain theoretical cleavage sites. A. Represents the fragment of protein D1 between amino acid positions 61 and 120, identified as SEQ ID NO: 3, and B. represents the fragment of protein D1 between amino acid positions 121 and 180, identified as SEQ ID NO: 4.

FIG. 4. Migration of the ST peptide identified as SEQ ID NO: 1 purified in polyacrylamide gel in denaturing conditions.

FIG. 5. a) Production of markers of migration to intestinal mucosa (integrin β7) and to skin (CLA) in enriched dendritic cells from human blood (LDCs). The conditions tested were the baseline (absence of signaling), 0.0, 0.1, 1.0 or 10 micrograms/milliliter of the ST peptide identified as SEQ ID NO: 1. b) the test carried out with this peptide alters neither the markers of migration to tissues (β7 and CLA), nor the molecules of the MHC of type II (HLA-DR) nor certain co-stimulatory molecules (CD40) or activating molecules (CD83) on enriched dendritic cells from human blood. Stimulation with lipopolysaccharide (LPS) was used as a control of stimulation with a pro-inflammatory bacterial component.

FIG. 8. From left to right, representations obtained by flow cytometry that represents populations of T cells stimulated with allogenic dendritic cells. Left panel: detection of viable cells by the "forward side scatter" technique. Central panel: identification of the marker DC3. Right panel: the stimulated T cells were identified by loss of the staining for CFSE derived from cell division.

FIG. 10. Flow cytometry diagrams showing changes in the production of the cytokines IL-10, TGFβ, IFNγ and IL-17 in T lymphocytes stimulated by enriched dendritic cells from blood (LDC) and pulsed with different concentrations of the ST peptide identified as SEQ ID NO: 1 (BP LDC) or lipopolysaccharide (LPS LDC). In all cases comparison was with the changes produced in the T cells at rest (resting T-cells), and using unstimulated LDCs (basal LDC).

FIG. 14. Flow cytometry diagrams representing the production of IL-10 and IL-12 in a donor whose dendritic cells of the colon mucosa displayed abnormal production of IL-12. These dendritic cells were incubated in the presence of the ST peptide identified as SEQ ID NO: 1 (+BP). In comparison with the baseline conditions (basal) the presence of the ST peptide identified as SEQ ID NO: 1 was capable of inducing the production of IL-10 and of blocking the production of IL-12.

BIBLIOGRAPHY

Adams et al. (2008) IgG antibodies against common gut bacteria are more diagnostic for Crohn's Disease than IgG against mannan or flagellin. *Am. J. Gastroenterol.* 103, 386-396

Feng and Elson (2010) Adaptive immunity in the host—microbiota dialog. *Muc. Immunol.* 4, 15-21

Lebeer et al. (2010) Host interactions of probiotic bacterial surface molecules: comparison with commensals and pathogens. *Nat. Rev. Microbiol.* 8, 171-84

Rescigno et al. (2001) Dendritic cells express tight junction proteins and penetrate gut epithelial monolayers to sample bacteria. *Nat Immunol.* 2, 361-367

Rijkers, G. T. et al. (2010) Guidance for substantiating the evidence for beneficial effects of probiotics: current status and recommendations for future research. *J. Nutr.* 140, 671S-676S Sánchez et al. (2008) Exported proteins in probiotic bacteria: adhesion to intestinal 25 surfaces, host immunomodulation and molecular cross-talking with the host. FEMS *Immunol. Med. Microbiol.* 54, 1-17

Sibbald and van Dijl (2009) Bacterial secreted proteins: secretory mechanisms and role in pathogenesis. Ed. Wooldridge, Caister Academic Press Turroni et al. (2010) Characterization of serpin-encoding gene of *Bifidobacterium breve* 210B. *Appl. Environ. Microbiol.* 76, 3206-3219

Zhu and Pau (2008) CD4 T cells: fates, functions, and faults. *Blood* 112, 1557-1569

EXAMPLES

The following specific examples that are provided in this patent document serve to illustrate the nature of the present invention. These examples are included solely for purposes of illustration and are not to be interpreted as limitations to the invention claimed herein. Therefore the examples described hereunder illustrate the invention without limiting the field of application thereof.

Identification of the Proteins Secreted by *Lb. plantarum* and of the ST Peptide Identified as SEQ ID NO: 1

*Lb. plantarum* is a mesophilic lactic acid bacterium that can be isolated from a large number of fermented foodstuffs, including vegetable and milk products (Tallon et al. (2003) Isolation and characterization of two exopolysaccharides produced by *Lactobacillus plantarum* EP56. *Res. Microbiol.* 154, 705-712). The capacity of some strains for surviving the conditions of the human gastrointestinal tract has meant that some researchers have been interested in its probiotic potential. Thus, the beneficial effects of some strains of *Lb. plantarum* on human health, currently marketed as probiotics (as is the case of strain 299v), have been demonstrated scientifically (de Vries, et al. (2006) *Lactobacillus plantarum*—survival, functional and potential probiotic properties in the human intestinal tract. Int. Dairy J. 16, 1018-1028).

Figure 1:
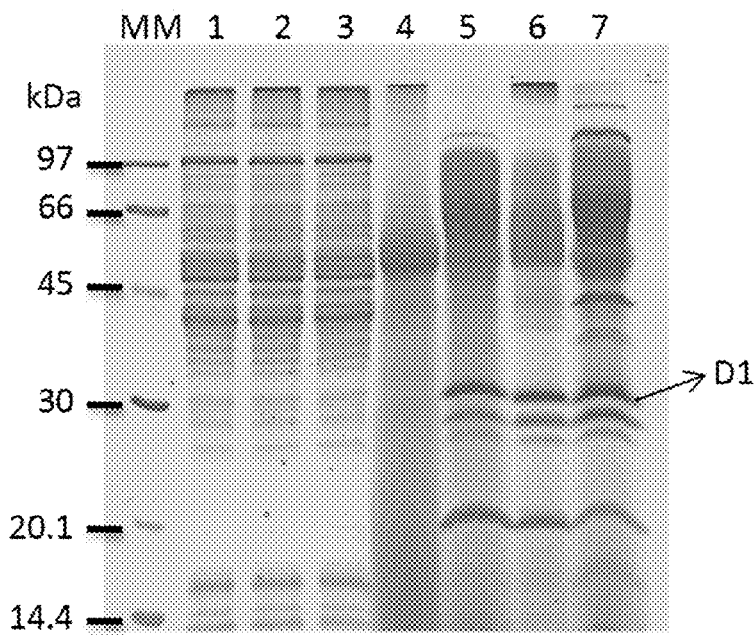
FIG. 1. Protein gel in denaturing conditions showing the total proteins and proteins secreted by 3 strains of *Lactobacillus plantarum*. Lanes 1-3: total proteins of strains NCIMB 8826, 299v and BMCM12. Lane 4: proteins present in the culture medium. Lanes 5-7: proteins secreted by strains NCIMB 8826, 299v and BMCM12. MM: marker of molecular weight of proteins (kDa).
Figure 2:
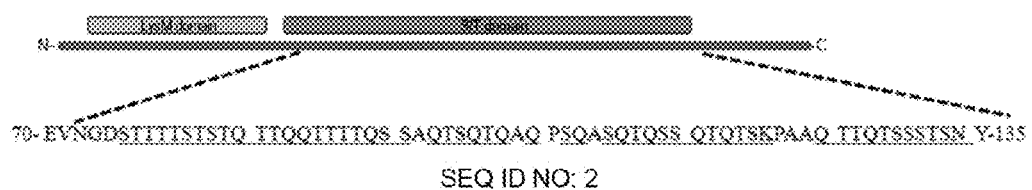
FIG. 2. A. Zone rich in serines and threonines present in the central zone of protein D1 identified as SEQ ID NO: 2, between amino acid positions 70 and 135, and B. Amino acid sequence of the ST peptide identified as SEQ ID NO: 1, described in the present patent. The amino acids underlined in SEQ ID NO: 1 represent the changes of the ST peptide relative to the central zone of protein D1 identified as SEQ ID NO: 2.

At present, there is growing interest in investigating the proteins secreted by probiotic bacteria, as they are potential mediators of intercellular communication between bacteria and cells of the host's immune system. As can be seen in FIG. 1, which shows the main proteins secreted by *Lb. plantarum* NCIMB 8826, *Lb. plantarum* 299v and *Lb. plantarum* BMCM12 (lanes 5, 6 and 7), there is relative similarity between the proteins secreted by different members of the species *Lb. plantarum*. The sequence of the ST peptide, whose sequence is shown in FIG. 2 identified as SEQ ID No: 1, is derived from the central zone of the protein designated D1 (GenBank identifying number gi|28270057) identified as SEQ ID No: 2, with some modifications and inclusions of amino acids that are shown underlined in SEQ ID NO: 1 (FIG. 2). This zone is characterized by its richness in the amino acids serine and threonine, from which its name is derived, and is characterized by the absence of cleavage sites for some of the most important proteases of the gastrointestinal tract (pepsin, trypsin and chymotrypsin) (FIG. 3).

Cloning and Purification of the ST Peptide Identified as SEQ ID NO: 1 (Verification of the Absence of Lipopolysaccharide)

The DNA sequence coding for the fragment ST (corresponding to the amino acid sequence marked in FIG. 2 as SEQ ID NO: 2), was cloned in *Lactococcus lactis* and was purified in a nickel affinity column according to standard protocols. This peptide is secreted to the culture supernatant, from where it can be isolated and purified, and is characterized by forming artifacts in agarose gels in denaturing conditions (SDS-PAGE), migrating to a size corresponding to about 100 kDa (FIG. 4). The sequence of the terminal amino of the peptide was verified by Edman degradation.

Regions rich in serine and threonine can be found in proteins encoded by many other lactic acid bacteria and in genera of the gastrointestinal tract, so that the conclusions derived from the present invention could be applied to ST peptides derived from other sequences of other microorganisms.

Interaction of the ST Peptide Identified as SEQ ID NO: 1 with Dendritic Cells

Since the ST peptides released by the intestinal proteases or by the proteases of the antigen presenting cells may be capable of influencing the function of the innate immune system associated with mucosae, we undertook an investigation of their interaction with the principal antigen presenting cells, the DCs. Firstly, absence of lipopolysaccharide in the samples of ST peptide identified as SEQ ID NO: 1 was verified using the chromogenic kit from Genscript. Our starting hypothesis was to consider that the ST peptide identified as SEQ ID NO: 1, produced in the intestinal environment or ingested with foodstuffs, might interact with the DCs of the intestinal mucosa, thus affecting the immune function.

Example 1

Interaction of the ST Peptide Identified as SEQ ID NO: 1 with Dendritic Cells Derived from Blood 1.1. Material and Methods The dendritic cells were obtained from healthy patients who had neither autoimmune diseases, nor inflammatory diseases nor allergies nor malignant tumors. These subjects had given their written consent for their blood to be used for scientific purposes. The peripheral blood mononuclear cells (PBMCs) were isolated by differential centrifugation in Ficoll-Paque Plus (Amersham Biosciences, Chalfont St. Giles, UK). The cellular fraction LDC (low-density cells) was obtained by overnight centrifugation in NycoPrepe™ solution. The cells present in this LDC fraction were HLA-DR positive in 98-100% of cases, with morphological characteristics typical of the DCs (Ng, et al. (2009). A novel population of human CD56+ human leukocyte antigen D-related (HLA-DR+) colonic lamina propria cells is associated with inflammation in ulcerative colitis. *Clin. Exp. Immuno*1.158, 205-218).

Half a million LDCs per milliliter were cultured in complete medium (Dutch modified RPMI 1640 (Sigma-Aldrich, Dorset, UK) containing 100 U/mL penicillin/streptomycin, 2 mM L-glutamine, 50 U/mL gentamicin (Sigma-Aldrich) and fetal bovine serum at 10% (v/v) (TCS cellworks, Buckingham, UK)). These cultures were carried out in the presence of the ST peptide identified as SEQ ID NO: 1 purified at concentrations of 10 µg/mL, 1 µg/mL and 0.1 µg/mL, and of LPS (100 ng/mL) (Sigma-Aldrich, St. Louis, USA) as positive control. The results were compared with parallel cultures without ST peptide identified as SEQ ID NO: 1 nor added LPS, acting as negative controls.

For the various experiments, labeling of the cells with the various antibodies (Table 1) was carried out in PBS supplemented with 1 mM EDTA and sodium azide at 0.02% (w/v) (FACS buffer). Labeling was carried out for 20 minutes in ice, in the dark. The cells were then washed with FACS buffer and were fixed with paraformaldehyde at 1% (v/v) in saline solution, and stored at 4° C. until acquisition of data in the flow cytometer. The negative controls used were isotype-matched antibodies without specificity, labeled with the same fluorochrome, which were obtained from the same company (isotype controls).

The flow cytometry data were obtained in a FACSCalibur cytometer (BD Biosciences), and the data were analyzed with the WinList 5.0 software (Verity, Me., US). The proportion of samples positive for a particular marker was determined relative to isotype controls. For quantification by histograms, an analysis was performed with the WinList software, in which the histogram of isotype staining was subtracted from the histogram of specific staining using normalized superenhanced $D_{max}$ (SED) substraction (Bagwell, C. B. (2005). Hyperlog—a flexible log-like transform for negative, zero, and positive valued data. Cytometry. 64, 34-42).

Intracellular Staining of Cytokines

The DCs were cultured for 4 hours in the presence/absence of monensin. Then they were stained for the surface markers as described above. Next they were fixed with LeucopermA, and permeabilized with LeucopermB before adding the intracellular staining antibodies. After incubation, the DCs were washed in FACS buffer, were fixed and were acquired as described above. The analysis was performed by the SED substraction detailed above, where the histogram of each cytokine of the DCs that had not been incubated with monensin were subtracted from the histogram of each cytokine of the DCs that had been incubated in the absence of monensin. This protocol has been extensively validated by our colleagues (Hart et al., (2005) Characteristics of intestinal dendritic cells in inflammatory bowel diseases. *Gastroenterology.* 129, 50-65) and makes it possible to quantify changes in the natural production of cytokines by the DCs in the absence of external stimuli such as PMA and/or ionomycin. Using this approach, the intracellular content of each cytokine is not determined. Instead, the changes induced in the production of cytokines in a temporal window of 4 hours (incubation time with monensin) are determined independently of the initial content of cytokines.

1.2. Results

As can be seen in FIG. 5 (panel A), the ST peptide identified as SEQ ID NO: 1 did not produce changes in the markers of migration of the DCs enriched with peripheral blood (integrin β7, intestinal mucosa marker and CLA, skin marker). Nor did the peptide produce changes in the induction of MHC molecules of type II (HLA-DR) or of certain co-stimulating molecules (CD40) or activation molecules (CD83) (FIG. 5, panel B). As can be seen in the latter, LPS (positive control) did induce overexpression in all of them.

Figure 6:
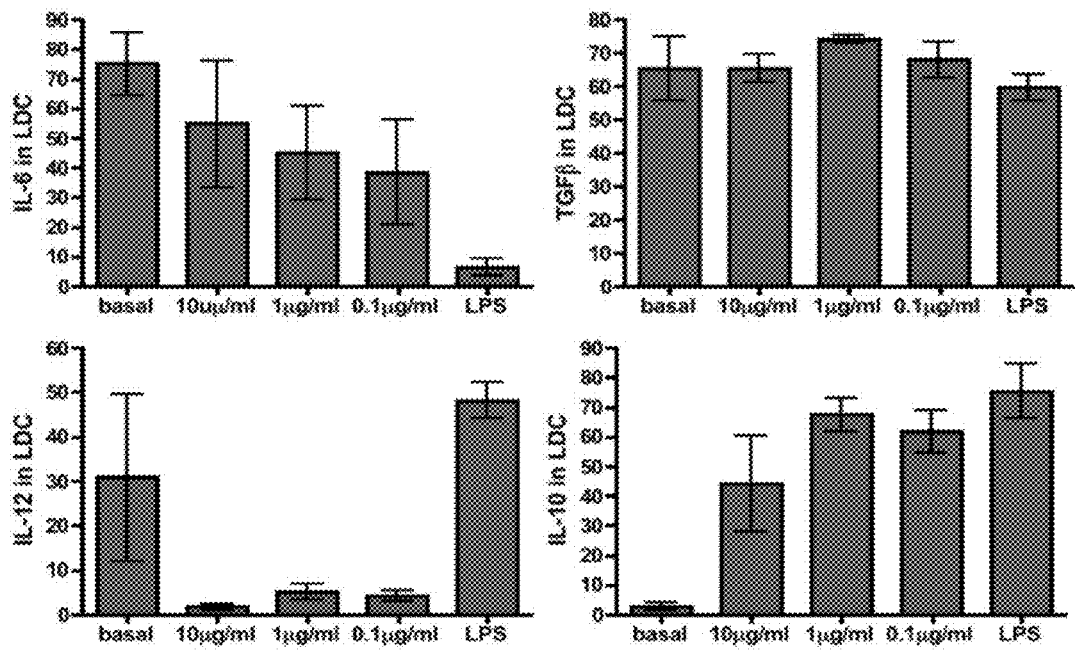
FIG. 6. Modification of the profile of production of cytokines measured in the cytoplasm of enriched dendritic cells from human blood induced by different concentrations of the ST peptide identified as SEQ ID NO: 1. Stimulation with LPS was used as a control of stimulation with a pro-inflammatory bacterial component. IL-6: interleukin 6, TGFβ: transforming growth factor beta, IL-10: interleukin 10, IL-12: interleukin 12.

Regarding the changes in the production of (intracellular) cytokines induced by the peptide in LDCs, this did not affect the regulatory molecule TGFβ, implicated in the control of cell growth, in cellular proliferation, and in processes of differentiation and apoptosis. Conversely, the ST peptide identified as SEQ ID NO: 1 induced a reduction in the synthesis of IL-6 (inducer of the generation of Th17 cells) and IL-12 (pro-inflammatory), and an increase in the synthesis of IL-10 (anti-inflammatory and homeostatic) (FIG. 6).

In conclusion, the presence of the ST peptide identified as SEQ ID NO: 1 in enriched dendritic cells from human blood (LDCs) means that these acquire a profile of production of regulatory cytokines, reducing the production of the pro-inflammatory cytokine IL-12 and increasing the production of the anti-inflammatory cytokine IL-10. The reduction in the synthesis of IL-6, with consequent theoretical reduction in the synthesis of type Th17 T cells, is also interesting since in the context of certain autoimmune and inflammatory diseases an increase of this cell type is observed (Stockinger and Veldhoen (2007) Differentiation and function of Th17 T cells. *Curr. Opin. Immunol.* 19, 281-286).

Example 2

Interaction of the ST Peptide Identified as SEQ ID NO: 1 with Dendritic Cells Obtained from Biopsy of Intestinal Mucosa Since the site of action of the ST peptide identified as SEQ ID NO: 1 would in principle be the intestinal mucosa, we decided to try to validate the experiments described in example 1 using DCs isolated from said location.

2.1. Material and Methods

Biopsies from the colon were obtained from three healthy patients, who had given their written consent to participate in this study (one woman and two men, age range 30-58 years). These patients had normal intestines, both macroscopically and histologically, and had been examined after reporting changes in intestinal transit or rectal bleeding. Once obtained, the biopsies were collected in complete medium cooled to 4° C. and were processed before the first hour counting from when they were obtained. The biopsies were incubated in *Hanks's balanced salt solution* (HBSS) (Gibco BRL, Paisley, Scotland, UK) containing 1 mM dithiothreitol (DTT) (Sigma-Aldrich) for 20 minutes. Next, they were incubated in a 1 mM solution of ethylenediaminetetraacetic acid (EDTA) in order to remove both the epithelial cells and the layer of mucus and its associated bacteria. The mononuclear cells of the lamina propria were extracted by digestion in the presence of collagenase D 1 mg/mL (Roche Diagnostics Ltd, Lewes, UK) in complete medium, which does not affect the phenotype or the function of the DCs (Hart et al. (2005) Characteristics of intestinal dendritic cells in inflammatory bowel diseases. *Gastroenterology,* 129, 50-65). The cellular suspensions of mononuclear cells of the lamina propria (200000 cells/mL) were incubated for 4 hours in the presence of the ST peptide identified as SEQ ID NO: 1 purified (10 µg/mL) and in the presence/absence, in its turn, of monensin, with their corresponding negative controls. The DCs of the lamina propria were identified by flow cytometry from the presence of the markers HLA-DR+ and CD3-CD14-CD16-CD19-CD34- (Hart et al. (2005) Characteristics of intestinal dendritic cells in inflammatory bowel diseases. *Gastroenterology,* 129, 50-65).

The remaining procedures followed in this example were the same as in section 1 of example 1.

2.2. Results

Figure 7:
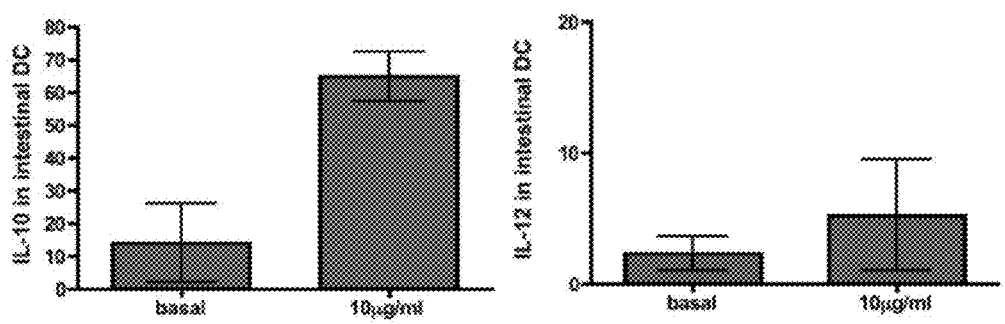
FIG. 7. Modification of the profile of production of the cytokines IL-10 and IL-12 measured in the cytoplasm of enriched dendritic cells from colon mucosa biopsies (intestinal DC).

Using the model of intestinal DCs, the two most interesting points described in example 1 could be confirmed, the increase in the production of IL-10 and the absence of any increase in the production of IL-12. At this point it has to be borne in mind that the DCs isolated from the intestinal mucosa of healthy individuals have very low levels of production of the pro-inflammatory cytokine IL-12 (FIG. 7).

Example 3

Interaction of Dendritic Cells Obtained from Blood Matured with the ST Peptide Identified as SEQ ID NO: 1 with T Lymphocytes 3.1. Material and Methods The T lymphocytes were obtained from peripheral blood mononuclear cells (PBMCs). The PBMCs, obtained from freshly drawn blood as described in example 1, were resuspended in MiniMACs buffer (PBS supplemented with bovine serum albumin 0.5% (w/v) and EDTA 2 mM). This suspension was enriched with T cells by removing the CD14 positive, CD19 positive and HLA-DR positive cells with immuno-magnetized beads (Miltenyi Biotech, Bisley, UK) following the manufacturer's instructions. A percentage of T cells of 94.91%±1.06 (mean±standard deviation) was obtained as the mean value of all the extractions/enrichments.

The T cells were labeled with 5-carboxyfluorescein diacetate succinimidyl ester (CFSE, Invitrogen Ltd, UK) according to the manufacturer's instructions. The T cells thus labeled ($4 \times 10^5$ cells per well) were incubated for 5 days with DCs at 0, 1, 2 or 3% in microtiter plates with U-shaped bottom. The proliferating T cells were identified and quantified by flow cytometry as those that contained a small amount of CFSE ($CFSE^{low}$) (FIG. 8).

The remaining flow cytometry protocols were carried out as described in section 1 of example 1.

3.2. Results

The fraction of T cells that were not put in contact with DCs (resting T cells) displayed a profile of "homing" (markers that indicate to which tissue they are directed) and of production of interleukins (IL-10, TGFβ, IFNγ, IL-17) characteristic of each donor. As was to be expected, both the absolute values of "homing" markers, and those of production of cytokines produced by LDCs (example 1) not conditioned with the ST peptide identified as SEQ ID NO: 1 or with LPS, were also different in each donor.

Figure 9:
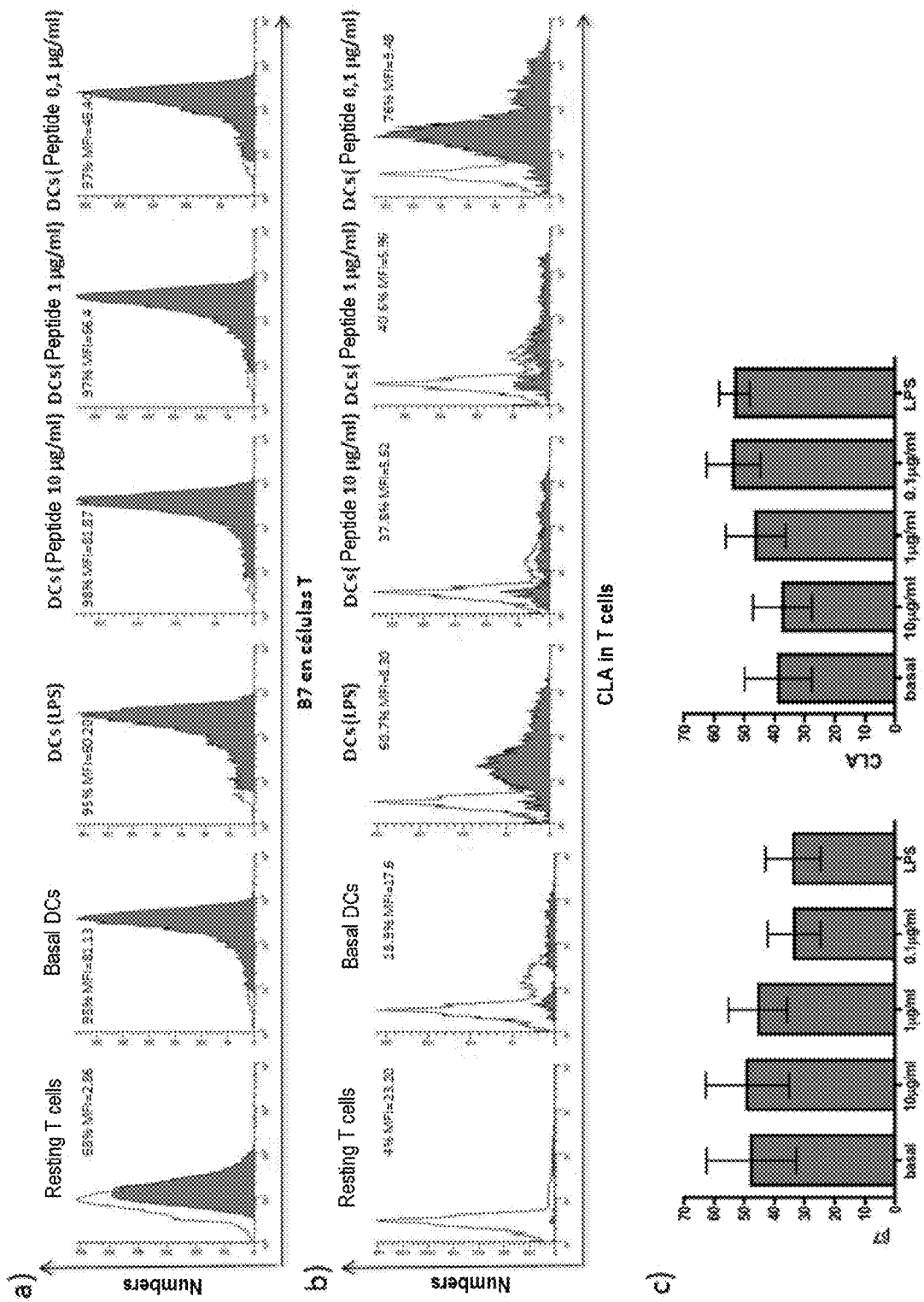
FIG. 9. Flow cytometry diagrams showing changes induced in T cells stimulated by enriched dendritic cells from blood (LDC) and exposed to the ST peptide identified as SEQ ID NO: 1 (LDC BP) or to lipopolysaccharide (LPS LDC). In all cases comparison was with the changes produced in the T cells at rest (resting T-cells), and using unstimulated LDCs (basal LDC). A) Changes in the levels of the marker of migration to intestinal mucosa integrin β7 induced by different concentrations of the ST peptide identified as SEQ ID NO: 1 (BP LDC) and of lipopolysaccharide (LPS LDC). B) Changes in the levels of the marker of migration to skin CLA induced by different concentrations of the ST peptide identified as SEQ ID NO: 1 (BP LDC) and of lipopolysaccharide (LPS LDC). C) Bar chart representation of the results of 3 independent experiments.

Despite this, the DCs incubated beforehand with the ST peptide identified as SEQ ID NO: 1 or with LPS (positive control), always induced the same profile of production of cytokines and of "homing" markers in the T cells from the various donors. Focusing on the DCs incubated with the ST peptide identified as SEQ ID NO: 1, these induced, in the T lymphocytes, a decrease in the marker of migration to intestinal mucosa integrin β7, whereas, conversely, the amount of marker CLA (marker of migration to skin) increased considerably (FIG. 9). Therefore, the DCs enriched with blood incubated in the presence of the ST peptide identified as SEQ ID NO: 1 imprint markers of migration to skin in the T lymphocytes. From the immunologic viewpoint, this can be interpreted as a mechanism of immune ignorance of the antigens present in the gastrointestinal tract. In this sense, the T cells, once in the skin, would never encounter the antigen against which they were selected in the intestinal mucosa, and are therefore inactive.

Figure 10:
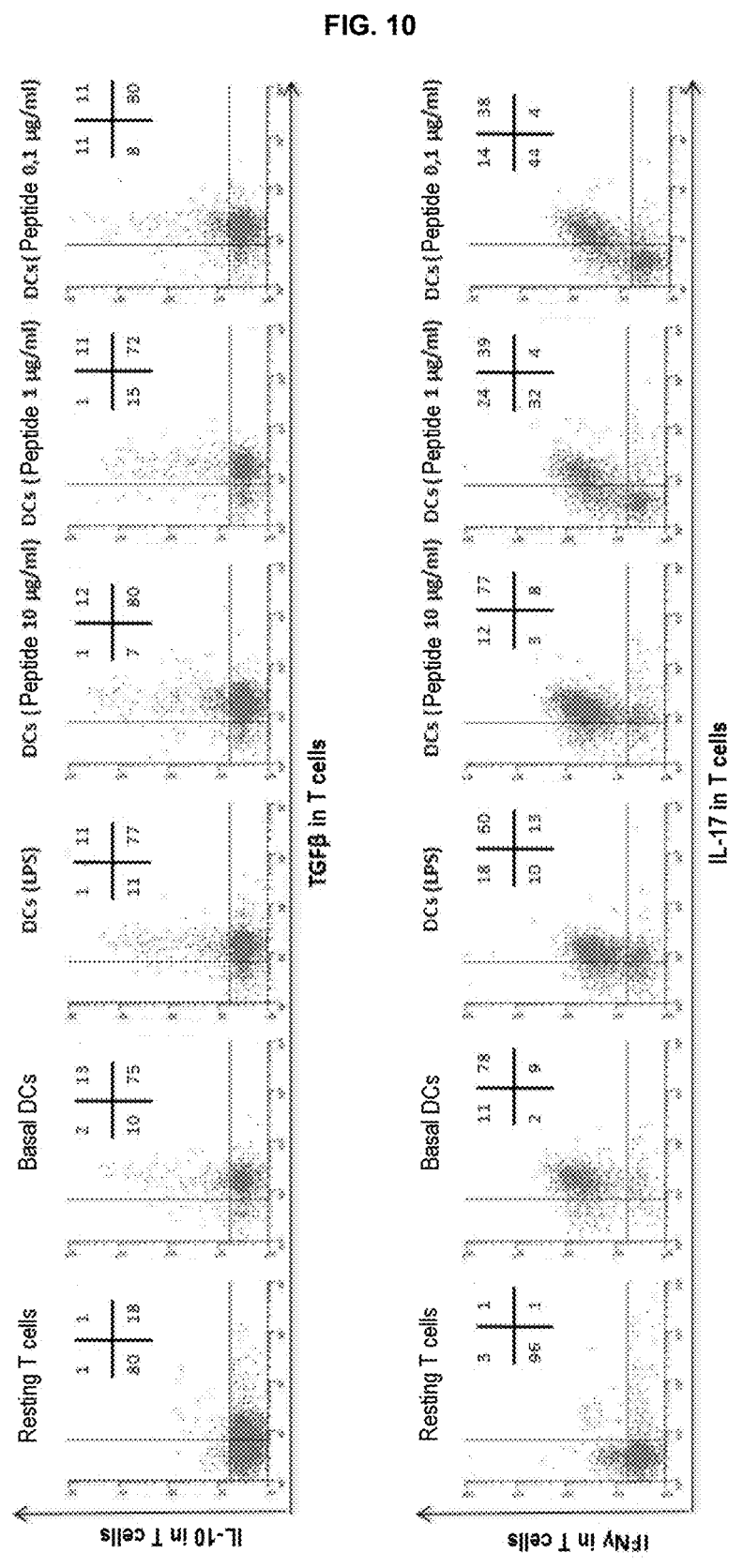
Figure 11:
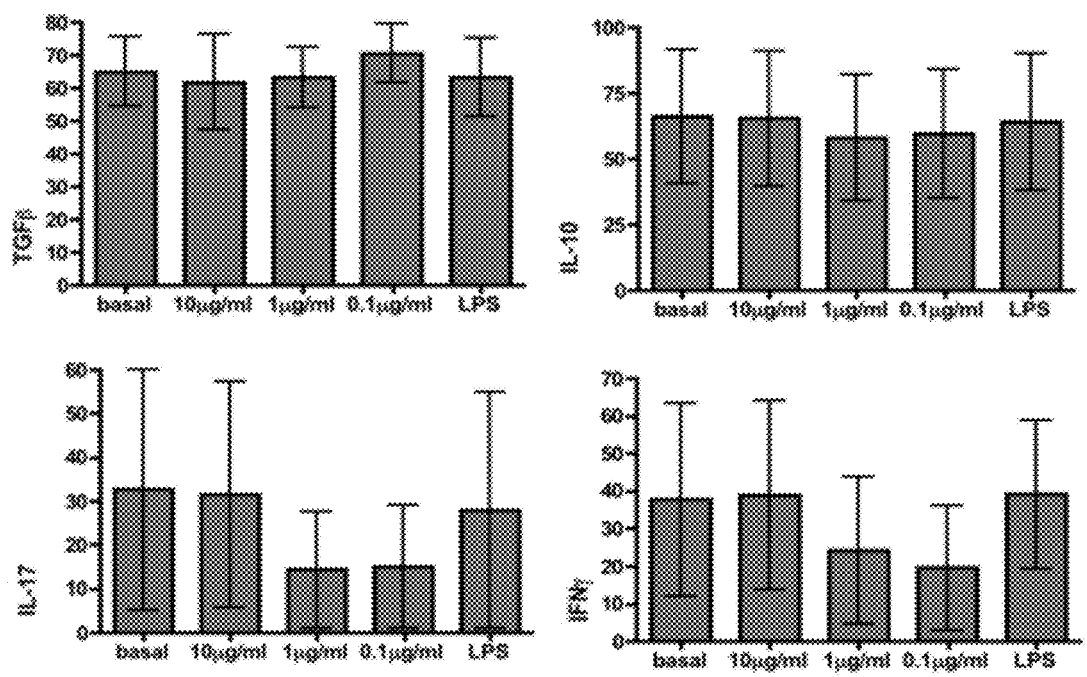
FIG. 11. Graphical representation of the data in FIG. 10 showing the values of 3 independent experiments and their deviations.

Moreover, the profile of production of cytokines in these same T cells (co-incubated with DCs that had previously been incubated with the ST peptide identified as SEQ ID NO: 1) differed in the sense that both the production of IFNy and of IL-17 decreased (FIGS. 10 and 11). Both cytokines are pro-inflammatory, and in the case of IL-17 (Th17 cells) it is known that its production by the T cells is greater in certain autoimmune and inflammatory diseases.

Therefore the T lymphocytes matured with DCs conditioned by the ST peptide identified as SEQ ID NO: 1 acquire a profile of production of non-pro-inflammatory cytokines and a profile of migration to skin.

Example 4

Figure 12:
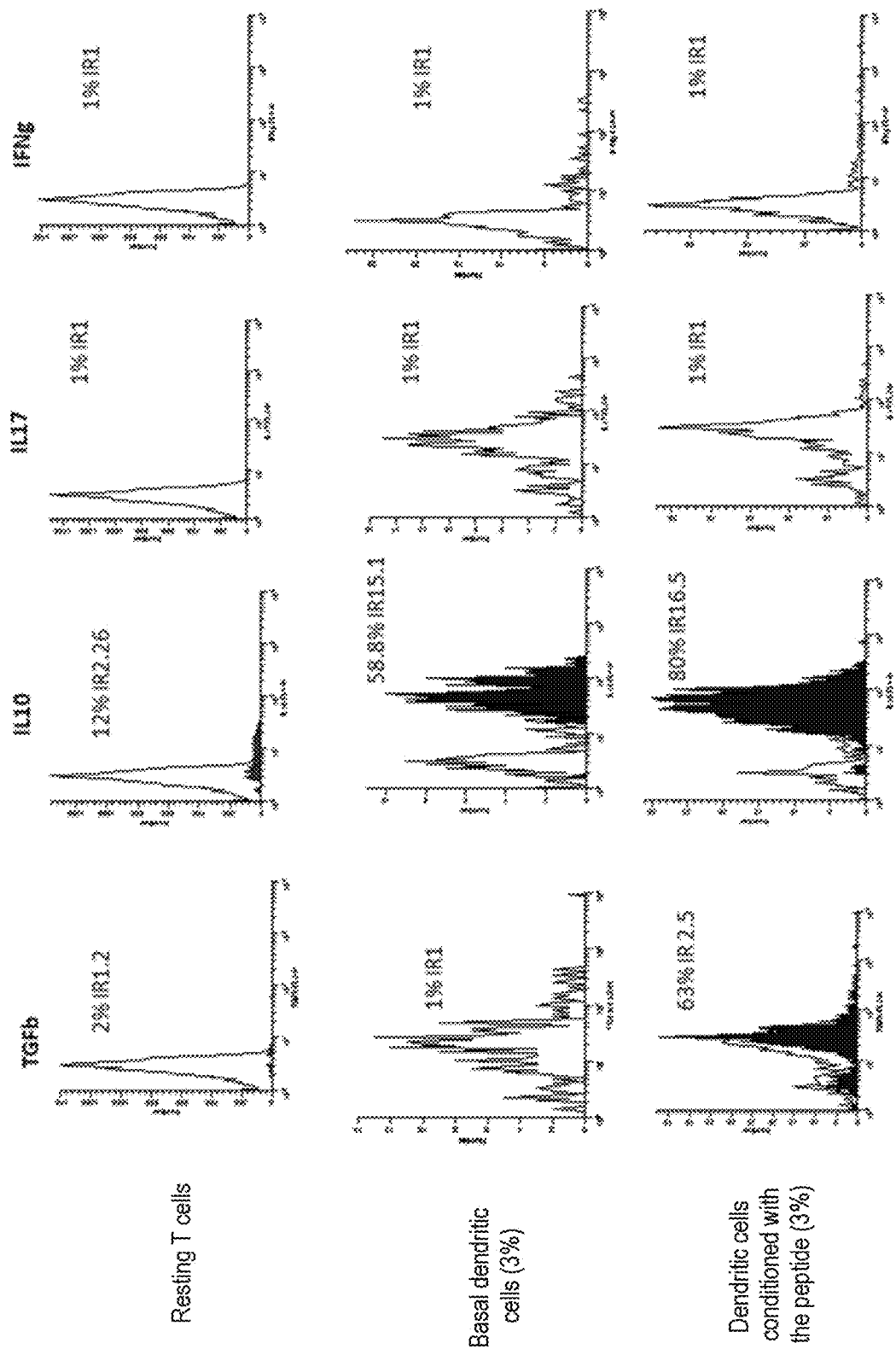
FIG. 12. Flow cytometry diagrams showing changes in the production of the cytokines TGFβ, IL-10, IL-17 and IFNγ in T lymphocytes stimulated by enriched dendritic cells from colon biopsies (gut DC) in the absence of stimulation (basal gut DC) (central panel) or pulsed beforehand with the ST peptide identified as SEQ ID NO: 1 (peptide gut DC) (bottom panel). The top panel shows the production of the same cytokines in T cells at rest (resting T cells).

Interaction of Dendritic Cells Obtained from Intestinal Mucosa Matured with the ST Peptide Identified as SEQ ID NO: 1 with Virgin T Lymphocytes This example is the same as the preceding example, except in this case DCs isolated from intestinal mucosa were used. As can be seen in FIG. 12, the intestinal DCs are already "homeostatic" in the sense that the profile of cytokines that they imprint on the T cells is to induce IL-10 (anti-inflammatory), whereas there is no increase in other interleukins (TGFβ, IL-17 and IFNγ). The DCs incubated with the ST peptide identified as SEQ ID NO: 1 induce an even greater increase in the production of IL-10 and in the production of TGFβ in the T cells (FIG. 12c).

Figure 13:
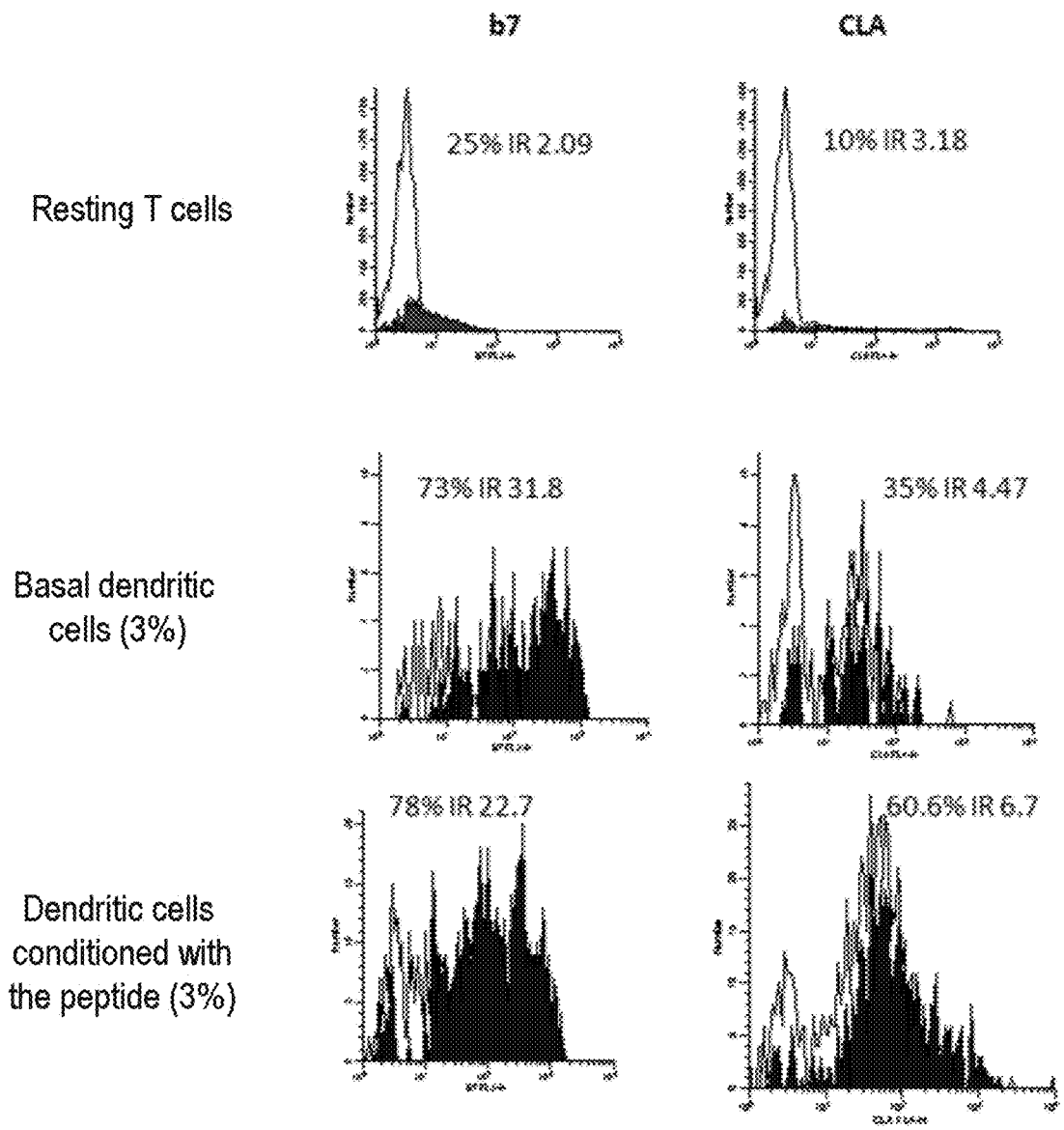
FIG. 13. Flow cytometry diagrams showing changes in the production of the markers of migration β7 (intestinal mucosa) and CLA (epithelial mucosa) in T lymphocytes stimulated with enriched dendritic cells from colon biopsies (gut DC) in the absence of stimulation (basal gut DC) (central panel) or pulsed beforehand with the ST peptide identified as SEQ ID NO: 1 (peptide gut DC) (bottom panel). The top panel shows the production of the same markers of migration in T cells at rest (resting T cells).

Finally, just as in the preceding example, the DCs conditioned by the peptide induce a greater number of lymphocytes that express the marker of migration to skin (FIG. 13) so that, once more, it is demonstrated that the ST peptide identified as SEQ ID NO: 1 would promote the process of immune ignorance.

Example 5

Potential Use of the ST Peptide Identified as SEQ ID NO: 1 in Inflammatory Bowel Disease, Autoimmune Diseases with Cutaneous Manifestations and Cosmetics One of the donors who gave written consent to donate a biopsy from the intestinal mucosa of the colon for our experiments had some DCs that produced unusually high levels of IL-12, the classical pro-inflammatory interleukin of the antigen presenting cells. As can be seen in FIG. 14, the ST peptide identified as SEQ ID NO: 1 completely cancelled the production of IL-12 in these dendritic cells, as well as increasing the production of the anti-inflammatory interleukin IL-10.

Although it is a single example, we suggest that the ST peptide identified as SEQ ID NO: 1 defined above could be included in programs of immunotherapy in the context both of inflammatory bowel disease and other inflammatory diseases, and in the context of autoimmune diseases that proceed with inflammatory symptoms.

The invention claimed is:

1. An ST peptide with immunomodulating and/or anti-inflammatory properties comprising an amino acid sequence having at least 95% homology with SEQ ID NO:1.

2. The ST peptide of claim 1 wherein the ST peptide is derived from a protein secreted by a lactic acid bacterium.

3. The ST peptide of claim 2 wherein the lactic acid bacterium is a strain of *Lactobacillus plantarum* selected from the following group: *Lb. plantarum* NCIMB 8826, *Lb. plantarum* 299V, and *Lb. plantarum* BMCM12.

4. The ST peptide of claim 1 comprising the amino acid sequence of SEQ ID NO:1.

5. A functional foodstuff comprising a therapeutically effective amount of the ST peptide of claim 1.

6. A pharmaceutical composition or medicinal product comprising a therapeutically effective amount of the ST peptide of claim 1.

7. A cosmetic comprising the ST peptide of claim 1.

8. The ST peptide of claim 1 wherein the amino acid sequence has a serine/threonine content of at least 50%.

9. The ST peptide of claim 1 wherein the peptide comprises at least a 30 kDa fragment that lacks a cleavage site for at least one intestinal protease.

10. The ST peptide of claim 9 wherein the intestinal protease comprises pepsin, trypsin, or chymotrypsin.

11. A method for treating an inflammatory intestinal disorder, the method comprising: administering to a subject a therapeutically effective amount of a composition comprising a polypeptide having at least 95% amino acid sequence homology with SEQ ID NO:1.

12. The method of claim 11 wherein the intestinal disorder comprises an inflammatory bowel disease or a celiac inflammation.

13. The method of claim 12 wherein the inflammatory bowel disease comprises Crohn's disease, ulcerative colitis, or pouchitis.

14. The method of claim 11 wherein the intestinal disorder is caused by an autoimmune disease or a disease caused by deregulation in the composition of the intestinal microbiota.

15. The method of claim 11 wherein a therapeutically effective amount of a composition is an amount effective to induce dendritic cells in the subject to produce an anti-inflammatory cytokine.

16. The method of claim 15 wherein the anti-inflammatory cytokine comprises IL-10.

17. The method of claim 11 wherein a therapeutically effective amount of a composition is an amount effective to inhibit dendritic cells in then subject from producing a pro-inflammatory cytokine.

18. The method of claim 17 wherein the pro-inflammatory cytokine comprises IL-12 or IL-6.

* * * * *